United States Patent
Morimoto

(10) Patent No.: US 12,428,315 B2
(45) Date of Patent: Sep. 30, 2025

(54) SYSTEM FOR ESTABLISHING A DIGITAL INTERCONNECTION BETWEEN VESSELS FOR COLLECTION OF MICRO-PLASTICS IN A SECURED WAY

(71) Applicant: Nobuyoshi Morimoto, Tokyo (JP)

(72) Inventor: Nobuyoshi Morimoto, Tokyo (JP)

( * ) Notice: Subject to any disclaimer, the term of this patent is extended or adjusted under 35 U.S.C. 154(b) by 111 days.

(21) Appl. No.: 18/541,780

(22) Filed: Dec. 15, 2023

(65) Prior Publication Data
US 2024/0286925 A1    Aug. 29, 2024

(30) Foreign Application Priority Data
Feb. 23, 2023  (IN) .............. 202311012492

(51) Int. Cl.
*C02F 1/00* (2023.01)
*B01D 21/00* (2006.01)
(Continued)

(52) U.S. Cl.
CPC .......... *C02F 1/008* (2013.01); *B01D 21/0084* (2013.01); *B63B 49/00* (2013.01);
(Continued)

(58) Field of Classification Search
CPC ........ C02F 1/008; C02F 1/24; C02F 2101/30; C02F 2103/007; C02F 2103/08;
(Continued)

(56) References Cited

U.S. PATENT DOCUMENTS

2016/0147223 A1* 5/2016 Edwards ................. B63B 79/40
701/2

FOREIGN PATENT DOCUMENTS

| CN | 106218825 A | * 12/2016 | ............. B63B 35/32 |
| CN | 111392803 A | * 7/2020 | ................ C02F 1/24 |
| KR | 2021135051 A | * 11/2021 | |

* cited by examiner

*Primary Examiner* — Kavita Stanley
(74) *Attorney, Agent, or Firm* — Muncy, Geissler, Olds & Lowe, P.C.

(57) ABSTRACT

The present invention provides a system for establishing a secured digital interconnection between vessels and optimizing a route of a vessel (1) for collecting maximum micro-plastics (30) from an aquatic environment, the system comprising: a collection unit (40) through which water containing micro-plastics (30) flows, a first set of sensors (60) operationally coupled to the collection unit (40) and configured to generate a first set of data by periodically measuring amount of micro-plastics (30) flowing in the collection unit (40), a second set of sensors (70) operationally coupled to the vessel (1) and configured to generate a second set of data by monitoring local environmental conditions, a communication device communicatively coupled to the vessel (1) and configured to authenticate ID, timestamp and location of other vessels and then communicate the first set of data and the second set of data between other vessels in the aquatic environment, a processing unit (90) coupled to the first set of sensors (60), the second set of sensors (70) and the communication device and configured to receive and analyze the first set of data, the second set of data and a communicated data received from the other vessels to predicts the optimum route for collecting maximum micro-plastics (30) from the aquatic environment.

10 Claims, 4 Drawing Sheets

(51) Int. Cl.
  *B63B 49/00*    (2006.01)
  *B63B 79/15*    (2020.01)
  *C02F 1/24*     (2023.01)
  *G01C 21/20*    (2006.01)
  *G01N 33/18*    (2006.01)
  *C02F 101/30*   (2006.01)
  *C02F 103/00*   (2006.01)
  *C02F 103/08*   (2006.01)

(52) U.S. Cl.
  CPC ................ *B63B 79/15* (2020.01); *C02F 1/24* (2013.01); *G01C 21/203* (2013.01); *G01N 33/1826* (2013.01); *C02F 2101/30* (2013.01); *C02F 2103/007* (2013.01); *C02F 2103/08* (2013.01); *C02F 2201/008* (2013.01); *C02F 2209/008* (2013.01)

(58) Field of Classification Search
  CPC .......... C02F 2201/008; C02F 2209/008; C02F 2209/006; C02F 1/001; B01D 21/0084; B63B 49/00; B63B 79/15; B63B 35/32; B63B 79/40; B63B 79/10; B63B 79/20; B63B 79/30; G01C 21/203; G01N 33/1826; B03D 1/082; B03D 1/1462; B03D 1/22; B03D 2203/008; E02B 15/10; H04L 63/0428; H04L 63/06; H04L 63/0876; H04L 67/104; H04L 67/12; H04L 2463/121
  See application file for complete search history.

SYSTEM FOR ESTABLISHING A DIGITAL INTERCONNECTION BETWEEN VESSELS FOR COLLECTION OF MICRO-PLASTICS IN A SECURED WAY

FIELD OF THE INVENTION

The present invention generally relates to prediction of location and collection of micro-plastics in an aquatic environment and optimizing a route of for vessels to collect maximum amount of micro-plastics yet maintaining the speed for reaching the destination.

BACKGROUND OF THE INVENTION

One of most prominent issues which the world is facing today is rapid increase in the amount of plastic waste in water bodies. The plastic waste is choking the oceans, threatening fragile ecosystems and killing the aquatic life. Many researchers have estimated that the amount of plastic in the water bodies is expected to double in the next 15 years, and by 2050 there could be more plastic than fish in the sea (by weight).

The micro-plastics are tiny plastics particles generally having the diameter of less than 5 mm. These micro-plastics are a result of both commercial product development such as cosmetics, textiles or the like and breakdown of larger plastics into smaller micro-plastics. The micro-plastics can be found everywhere in the water bodies, the deep oceans, the beaches, in Arctic snow and in Antarctic ice. These micro-plastics could take decades or more to degrade fully.

Every species of organisms living on the Earth has some level of exposure to micro-plastics. The micro-plastics have been detected even in the zooplanktons which are among the smallest marine creatures. These micro-plastics are getting swallowed by fishes and other sea creatures directly or indirectly and ending up in our food chain. The same is also expected to have adverse effects on the human health.

As vessel transport is responsible for a large portion of world commerce, it will be advantageous to developing a system which can be deployed on to the vessel, assisting in collection of micro-plastics from the aquatic environment and further providing an optimized route on which the vessel can collect maximum amount of micro-plastics without getting delayed in reaching their destination.

In view of the above limitations of the current technologies, there exists a need to develop a system which can optimize a route of a vessel in real time so that the vessel can collect maximum amount of micro-plastics without getting delayed in reaching destination.

Thus, the above-described deficiencies of conventional approaches including devices/products and methods thereof, are merely intended to provide an overview of some of the problems of conventional approaches and are not intended to be exhaustive. Other problems with conventional approaches, and methods and their corresponding benefits of the various non-limiting embodiments described herein may become further apparent upon review of the following description.

SUMMARY OF THE INVENTION

The following presents a simplified summary of the invention to provide a basic understanding of some aspects of the invention. This summary is not an extensive overview of the present invention. It is not intended to identify the key/critical elements of the invention or to delineate the scope of the invention. Its sole purpose is to present some concept of the invention in a simplified form as a prelude to a more detailed description of the invention presented later.

It is therefore the objective of the present invention to develop a system which can be attached to any vessel, thereby enabling the vessel to collect micro-plastics from an aquatic environment.

Another objective of the present inventive is to develop a system which can optimize a route of a vessel in real time so that the vessel can collect maximum amount of micro-plastics without getting delayed in reaching destination.

Further, another objective of the present invention is to develop a vessel which communicates with other vessel and share data among them in a peer to peer (P2P) communication through a secured way by confirming ids, timestamps, longitudes and latitudes bilaterally in real time.

Accordingly, in an aspect, the present invention provides a system for establishing an interconnection between vessels to provide an optimized and efficient route for a vessel, the system comprising: a collection unit through which water containing micro-plastics flows, a first set of sensors operationally coupled to the collection unit and configured to generate a first set of data by periodically measuring amount of the micro-plastics flowing in the collection unit, a second set of sensors operationally coupled to the vessel and configured to generate a second set of data by monitoring local environmental conditions, a communication device communicatively coupled to the vessel and configured to communicate the first set of data and the second set of data between other vessels in an aquatic environment, a processing unit coupled to the first set of sensors, the second set of sensors and the communication device, wherein the processing unit configured to receive, analyze the first set of data, the second set of data and a communicated data received from the other vessels to predict the optimum route for efficiently collecting maximum amount micro-plastics from the aquatic environment.

Accordingly, in another aspect, the present invention provides an air bubble generation unit coupled to the vessel and configured to generate air bubbles, wherein the micro-plastics adhere to the air bubbles generated by the air bubble generation unit, a purifying unit coupled to the collection unit and configured to separate the micro-plastics from the air bubbles for collecting separated micro-plastics.

Accordingly, in another aspect, the present invention provides the environmental conditions comprise local tidal strength, local tidal currents, local tidal direction, sunlight intensity, water temperature, water salinity, local wind speed, local wind direction, barographic pressure, amount of rainfall.

Accordingly, in another aspect, the present invention provides a display unit operationally coupled to the processing unit and configured to display the optimum route of the vessel, location of other vessels and their optimum routes.

Accordingly, in another aspect, the present invention provides a testing unit coupled to the collection unit, wherein the testing unit configured to collect a sample of the water flowing through the collection unit for testing chemical composition, virus and microorganisms present in the water.

Accordingly, in another aspect, the present invention provides a method for establishing an interconnection between vessels to provide an optimized and efficient route for a vessel, the method comprising: flowing water containing micro-plastics adhered to air bubbles through a collection unit, generating a first set of data at a first set of sensors operationally coupled with the collection unit, generating a second set of data at a second set of sensors operationally coupled with the vessel, communicating the first set of data and the second set of data among other vessels in the aquatic environment, receiving and analyzing at a processing unit, the first set of data, the second set of data, and a communicated data received from other vessels, and predicting at the processing unit, the optimum route for collecting maximum micro-plastics from the aquatic environment.

Accordingly, in another aspect, the present invention provides the first set of sensors configured to periodically measure amount of micro-plastic flowing in the collection unit.

Accordingly, in another aspect, the present invention provides the second set of sensors configured to monitor local environmental conditions.

Accordingly, in another aspect, the present invention provides the steps of transmitting an interrogation signal and ID of the vessel from a communication device disposed on the vessel, receiving the interrogation signal and ID of the vessel by other vessel in the aquatic environment, authenticating the ID of the vessel by comparing the ID with prestored IDs in a data storage memory disposed on the other vessel, responding to the interrogation signal upon authentication by transmitting a confirmation ID of the other vessel, authenticating the confirmation ID received from the other vessel by comparing with stored IDs in a data storage memory disposed in the vessel, encrypting data of the first set of sensors, the second set of sensors, location of the vessel and a timestamp done by a processing unit of the vessel and generating a key, sending the key followed by the encrypted data to the other vessel, decrypting the encrypted data by a processing unit disposed on the other vessel by using the key, encrypting data of a first set of sensors, a second set of sensors, location of the other vessel and a timestamp done by the processing unit of the other vessel and generating another key, sending the another key followed by encrypted data to the vessel, decrypting the encrypted data by the processing unit disposed on the vessel by using the another key.

Other aspects, advantages, and salient features of the invention will become apparent to those skilled in the art from the following detailed description, which, details the invention in different embodiments.

BRIEF DESCRIPTION OF THE DRAWINGS

While the specification concludes with claims that particularly point out and distinctly claim the invention, it is believed that the advantages and features of the present invention will become better understood with reference to the following more detailed description of expressly disclosed exemplary embodiments taken in conjunction with the accompanying drawings. The drawings and detailed description which follow are intended to be merely illustrative of the expressly disclosed exemplary embodiments and are not intended to limit the scope of the present invention as set forth in the appended claims. In the drawings:

DETAILED DESCRIPTION OF THE INVENTION

Call Out List

1 Vessel
10 Air Bubble Generating Unit
20 Air Bubbles
30 Micro-plastics
40 Collection Unit
41 Vertical Tube
42 Valves
43 Weir System Tank
43a First Tank
43b Second Tank
50 Purifying Unit
60 First set of Sensors
70 Second set of Sensors
81 Wi-Fi Antenna
82 Transceiver
83 GPS Module
84 Data Storage Memory
85 Power Supply
86 Motors
90 Processing Unit
100 Display unit
S1 First vessel in an exemplary embodiment
S2 Second vessel in an exemplary embodiment
S3 Third vessel in an exemplary embodiment
S4 Fourth vessel in an exemplary embodiment
SR1 Route of first vessel to reach point B from point A
SR2 Route of second vessel to reach point D from point C
SR3 Route of third vessel to reach point F from point E
SR4 Route of fourth vessel to reach point H from point G
OPR1 Optimum route for the first vessel
OPR2 Optimum route for the third vessel The exemplary embodiments described herein detail for illustrative purposes are subject to many variations in the structure and configuration. It should be emphasized, however, that the present invention is not limited to a particular composition as shown and described herein. It is understood that various omissions and substitutions of equivalents are contemplated as circumstances may suggest or render expedient, but these are intended to cover the application or implementation without departing from the scope of the claims of the present invention. Also, it is to be understood that the phraseology and terminology used herein is for the purpose of description and should not be regarded as limiting.

The use of terms "including," "comprising," or "having" and variations thereof herein are meant to encompass the items listed thereafter and equivalents thereof as well as additional items.

Further, the terms, "an" and "a" herein do not denote a limitation of quantity, but rather denote the presence of at least one of the referenced item.

Furthermore, the term "may" herein is used in a permissive sense (i.e. meaning having the potential to), rather than the mandatory sense, (i.e. meaning must).

Furthermore, the term "first", "second", and the like, herein do not denote any order, ranking, quantity, or importance, but rather are used to distinguish one element from another.

Furthermore, the term "vessel" herein is used to represent a watercraft used for travel on water. It may be but not limited to a ship or a boat.

Furthermore, the term "aquatic environment" herein is used to represent a water body for example: river, sea, ocean etc.

The present invention provides design of a system which enables a vessel to collect micro-plastics from an aquatic environment. Further, the system establishes a secured digital interconnection between vessels and provides an optimized route for a vessel to collect maximum amount of micro-plastics from the aquatic environment.

An exemplary embodiment of the present invention will be described with reference to the attached drawings.

Figure 1:
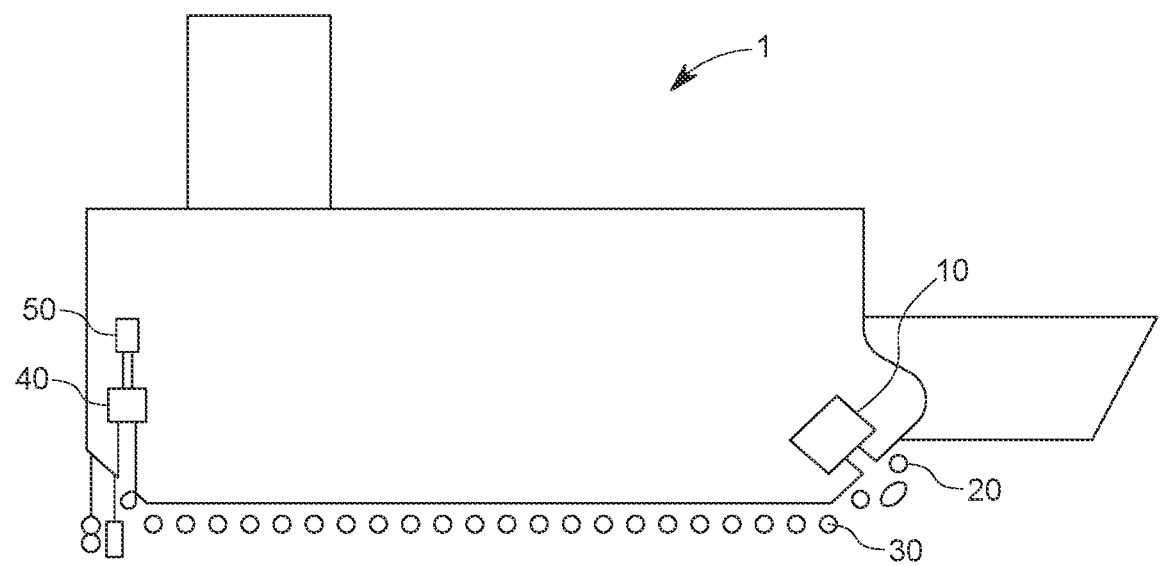
FIG. 1 illustrates a schematic diagram of a vessel for collecting micro-plastics from an aquatic environment as adopted in an embodiment of the invention.

FIG. 1 is a schematic diagram of a vessel 1 for collecting micro-plastics 30 from an aquatic environment adopted in an embodiment of the invention. The vessel 1 may be but not limited to a cargo ship, a passenger ship, a defense ship, a research ship or a fishing ship. The vessel 1 may comprises a bow section. The bow section may have a pair of extended arms coupled to a fore part of the vessel 1 and configured to generate air bubbles 20 naturally by collision of wave with a bow and inner wall of the pair of extended arms in a confined space between the pair of extended arms. Due to hydrophobic nature of the micro-plastics 30, the latter may get adhered to the air bubbles 20.

Additionally, an air bubble generating unit 10 may be provided on the vessel 1 which may be operationally coupled to the bow of the vessel 1. The air bubble generating unit 10 may comprise an air blower, an air compressor or any other dedicated system may use to create air bubbles 20. The air bubble generating apparatus may be configured to provide additional air bubbles 20 in the confined space between the pair of extended arms.

The micro-plastics 30 adhere to the air bubble may flow with the water from the bow area to a collection unit 40 provided on a bottom of the vessel 1. The micro-plastics 30 adhered to the air bubble may flow upward in the collection unit 40 due to buoyant forces. Rest of the water along with any marine life will flow through the collection unit 40.

A purifying unit 50 may be provided coupled to the collection unit 40. The purifying unit 50 may separate micro-plastics 30 from the air bubbles 20 and collects the separated micro-particle. The purifying unit 50 may comprise a simple filter like an active carbon filter or a fine mesh filter not allowing anything above 5 mm to pass through or a complicated system like Dyson vacuum cleaner which may have a drum or vacuum bin on which the microparticles adhered with the air bubble goes into the top corner of a drum or vacuum bin, and the angle it enters the bin causes it to Centrifugal forces spiral around, creating centrifugal force. This force causes the air bubbles 20 to burst and the micro-particles to spin out and fall to the bottom of the bin. The collected micro-plastics 30 may be removed on reaching to destination shore by empty the collected micro-plastics 30 or by an aerial vehicle (e.g., a drone) taking away the collected micro-plastics 30, etc. In another embodiment, the collected micro-plastics 30 may get burn on the vessel 1 by using ultrasonic waves or microwaves.

In another embodiment of the present invention, the air bubble generating unit 10 may be provided ahead of the collection unit 40. The air bubble generation unit may be configured to provide air bubbles 20 so that the microplastics 30 may adhere to the air bubbles 20 before reaching to the collection unit 40.

Figure 2:
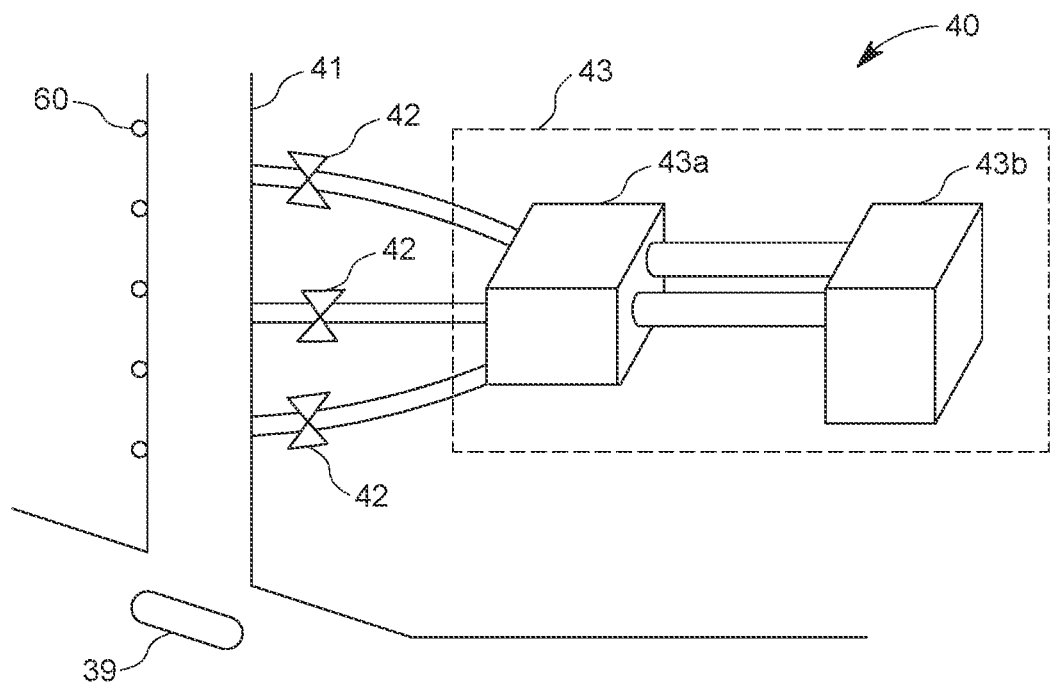
FIG. 2 illustrates a schematic diagram of a collection unit as adopted in an embodiment of the invention.

FIG. 2 is a schematic view of the collection unit 40 adopted in an embodiment of the invention. The collection unit 40 may comprises a fin 39, a vertical tube 41, valves 42 and weir system tanks 43. Distance between the bottom of the vessel 1 and the fin 39 may be keep narrow so that only micro-plastics 30 may flow through it and the larger particles of plastics or any other material may not enter between the bottom of the vessel 1 and the fin 39. This way, the fin 39 may separate large non related micro-plastics to flow outside of the collection unit. The distance between the bottom of the vessel 1 and the fin 39 may be kept 1 cm or less. A filter may be used as the fin 39 which may allow the microplastics 30 to pass through the filter and prevents anything larger to enter into bottom of the vertical tube 41.

The vertical tube 41 may be coupled with the bottom of the vessel 1. Further, light weight micro-plastics 30 adhered to air bubbles 20 may rise upwards in the vertical tube 41 along with some water. The amount of water in the vertical tube 41 may vary depending upon the movement of waves. The micro-plastics 30 being light in weight may float and accumulate on top of the water level. The material for vertical tube 41 may be selected from but not limited to transparent plastic and glass. The accumulation of microplastics 20 may be visible through the vertical tube 41. Further, a first set of sensors 60 may be coupled to the vertical tube 41 and configured to measure the water level in the vertical tube 41 and height column of the accumulated micro-plastics 30. Further, the cross sectional area of the vertical tube, the volume of the micro-plastics 30 may be calculated by using following formula:

$V=\pi r^2 h$,

Wherein V is volume of the micro-plastics 30, r is the radius of the vertical tube 41, and h is and height column of the accumulated micro-plastics in the vertical tube 41.

The valves 42 may be coupled to the vertical tube 41 and may be configured to open and close periodically. The valves 42 may be coupled with the weir system tanks 43. In close system, the valves 42 do not allow micro-plastics 30 adhered to the air bubbles 20 and water to flow through the vertical tube 41 to the weir system tanks 43. In this condition, the micro-plastics 30 may accumulate on top of the water level in vertical tube 41 and the volume of the micro-plastics 30 may be calculated using the above formula. When the volume of the micro-plastics 30 reaches a predetermined level, the valves 42 open up. In an open condition, the valves 42 may allow micro-plastics 30 adhered to the air bubbles 20 and water to flow from the vertical pipe 41 to the weir system tanks 43.

The weir system tanks 43 may comprises a first level tank 43a and a second level tank 43b. The first level tank 43a may be coupled with the valves 42 and configured to receive the micro-plastics 30 adhered to the air bubbles 20 and water. The second level tank 43b may be coupled to the first level tank 43a. The first level tank may comprises a hole through which the water will flow out of the first level tank into the aquatic environment. Flow rate in the first level tank 43a may be adjusted by the valves 42 and dimension of the hole in such a way that a constant level of water is maintained and the floating micro-plastics 30 may get skimmed to the second level tank 43b. A mechanical weighing machine is provided, coupled to the second tank 43b and configured to measure the weight of the collected micro-plastics 30 in the second tank 43*b*. The reading of the mechanical weighing machine may be compared with the volume of the micro-plastics 30 measured by the first set of sensors 60. Thus, the amount of the micro-plastics 30 may be verified and in case of any error, it may be spotted easily.

During the open condition, the valves 42 remain open and the micro-plastics 30 may get accumulated in the second level tank 43*b*. During that interval, the amount of the micro-plastics 30 collected in the second level tank 43*b* may be measured by the mechanical weighting machine. Once the opening interval passes (during the closed condition), the valves 42 close and the collected micro-plastics 30 from the second level tank 43*b* may be transferred to the purifying unit 50. Further, an air may be blown in the weir system tanks 43 to clean them and get ready for next batch of micro-plastics 30.

In an embodiment of the present invention, the vessel 1 may comprises a testing unit. The testing unit may be coupled to the weir system tanks 43 and collects a sample of water flowing through the weir system tanks 43. The testing unit may be configured to test chemical composition and micro-organisms present in the water. The testing unit may test various parameters like temperature, salinity, pH value, nitrates, phosphates, bio-chemical oxygen demand and micro-organisms present in the water. The testing unit may provide data regarding the various parameters of chemical composition and micro-organism which may be used for further analysis of condition of the aquatic environment and discovery of potential virus unknown to scientist and may cause pandemic by sampling in mass scale on surface of the aquatic environment.

The first set of sensors 60 may be coupled to the vertical tube 41 of the collection unit 40. The first set of sensors 60 may be selected from but not limited to infra-red sensors, ultrasonic sensors, optical sensors, CCD sensors, CMOS sensors etc. The first set of sensors 60 may be configured to periodically measure amount of micro-plastics 30 flowing in the collection unit 40 and generates a first set of data. The first set of data may include a time series data of periodically measured amount of micro-plastics 30 flowing in the collection unit 40. By doing it periodically, it can have a big data to confirm the area of clusters of micro-plastics in the aquatic environment to assist understanding the most effective route to collect micro-plastic 20 among many vessels.

Additionally, the vessel 1 may comprises a second set of sensors 70. The second set of sensors 70 may be placed at different places on the vessel 1. For example: one group of the second set of sensors 70 among the second set of sensors 70 may be placed at the bottom of the vessel 1 and other group of the second set of sensors 70 may be placed at deck of the vessel 1. The second set of sensors 70 may be configured to monitor environmental conditions. The environmental conditions may comprises but not limited to local tidal strength, local tidal currents, local tidal direction, sunlight intensity, water temperature, water salinity, local wind speed, local wind direction, barographic pressure, amount of rainfall. The second set of the sensors may comprises but not limited to dynamic pressure sensors, thermal flow sensors, ultrasonic flow sensors, vortex-shedding sensors, digital flow sensors, air flow sensors, barograph, barometer, coriolis mass flow sensors, phototransistors, photoresistors, and photodiodes, salinity sensors, thermistors, thermocouples, RTDs, and doppler radar sensor etc. The second set of sensors 70 may generate a second set of data. The second set of data may comprises a time series data of the environmental conditions.

The micro-plastics 30 are very small particles of plastics having a diameter less than 5 mm. The micro-plastics 30 have very light weight and can be easily drifted in any direction with the wind and water flow, thus location of the micro-plastics 30 may be depend upon the local environmental conditions. Therefore, monitoring of the environmental condition may be required to predict the location of the micro-plastics 30.

In an embodiment of the present invention, the vessel 1 may comprises a communication device. The communication device may be configured to communicate the first set of data and the second set of data with other vessels. The communication device may comprises a transceiver 82, a power supply 85, a data storage memory 84, and a Wi-Fi antenna 81. The transceiver 82 may be coupled to the antenna 81, the first set of sensors 60 and the second set of sensors 70. The transceiver 82 may be configured to authenticate and then send the first set of data and the second set of data to the other vessels. Further, the transceiver 82 may also be configured to authenticate and then receive the first set of data and the second set of data from the other vessels. The data storage memory 84 may be configured to store the data received from the first set of sensor 60, the second set of sensors 70 and a communicated data received from other vessels. Further the data storage memory 84 may stores IDs and private keys of all vessels. Medium for communication may be infrared, microwave, radio frequency (RF), wireless PAN, wireless LAN, wireless ad hoc network, cellular network, Wi-Fi, satellite communication and the like, sharing data among the vessels at 5G, 6G or at a faster data transmission speed. If the vessels are closer say 30 miles away from each other, the communication device may use Wi-Fi or some other medium of communication for near range communication. If there is no vessel in the vicinity of the vessel 1, let assume two vessels are 100 miles apart, for sharing the information the communication device may use satellite to communicate.

Figure 3:
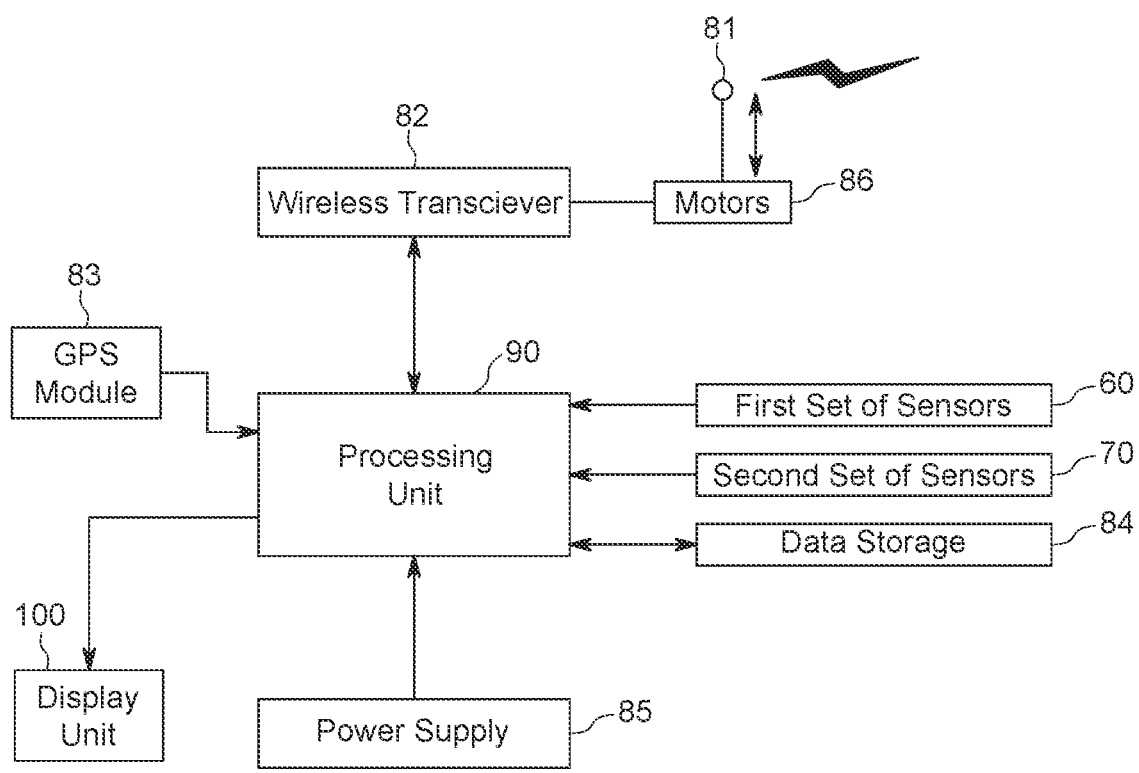
FIG. 3 illustrates a block diagram of a processor receiving data from a first set of sensors, a second set of sensors and other vessels as adopted in an embodiment of the invention.

FIG. 3 is a block diagram of the system receiving data from a first set of sensors 60, a second set of sensors 70 and other vessels as adopted in an embodiment of the invention. In an embodiment of the present invention, the vessel 1 may comprises a processing unit 90. The processing unit 90 may be coupled to the first set of sensors 60, the second set of sensors 70, the transceiver 82, the data storage memory 84, and the power supply 85. In some embodiments, the vessel 1 may also include one or more motors 86 controlled by the processing unit 90 and/or the transceiver 82. The motors 86 may be configured to extend a telescopic boom to give the antenna 81 more height. The processing unit 90 may be configured to cause motor to retract antenna 81 in an event that the winds reach a predetermined level of severity (e.g., ocean Storms or hurricanes). The processing unit 90 may be configured with hysteresis to keep the antenna 81 retracted for a predetermined amount of time before re-extending the antenna 81 to prevent the antenna 81 from being repeatedly extended and extracted in gusting wind conditions.

In an embodiment of the present invention, the vessel 1 may be configured with a direction sensor and/or GPS module 83. In such installations, the processing unit 90 may be configured to use the GPS module 83 to determine current position of the vessel 1. Further, the vessels may communicate the current position of the vessels among themselves. Thus, each vessel may have information of location of other vessels. In another embodiment, vessel 1 may be configured to maintain a database of other vessel's positions based on GPS data from their GPS modules 83 in the data storage memory 84.

In an embodiment of the present invention, the processing unit 90 may be coupled to the first set of sensors 60, the second set of sensors 70, the communication device and the data storage memory 84. The processing unit 90 may receive the first set of data from the first set of sensors 60. The processing unit 90 may receive the first set of data in real time. The processing unit 90 may analyze the first set of data and records the amount of micro-plastics 30 collected in the collection unit 40. The processing unit 90 may also record the location at which micro-plastics 30 are collected by using GPS module 83. Further, the processing unit 90 may receive the second set of data from the second set of sensors 70. The processing unit 90 may analyze the first set of data and the second set of data to predict the location and amount of the micro-plastics 30 in the aquatic environment. The processing unit 90 may utilize an Artificial Intelligence (AI) model.

In an embodiment of the present invention, the processing unit 90 may cause the communication device to transmit an interrogation signal and an ID from a communication device disposed on the vessel 1. The interrogation signal may be received by other vessel (Let's assume vessel 2) floating/sailing in the aquatic environment. The vessel 2 may authenticate the ID of the vessel 1 by comparing it with stored IDs in a data storage memory disposed on the vessel 2 and upon authentication of the ID may respond to the interrogation signal by transmitting a confirmation ID. The processing unit 90 disposed on the vessel 1 may authenticate the confirmation ID received from the vessel 2 by comparing with stored IDs in the data storage memory 84. Upon the authentication of the confirmation ID of the vessel 2, the processing unit 90 may encrypt data related to the predicted location of the micro-plastics 30, amount of the micro-plastics 30, location of the vessel and a timestamp and generate a key. A new key may be generate when the processing unit 90 may encrypt a new set of data. The key may be send to the vessel 2 followed by the encrypted data through the communication device disposed on the vessel 1. The encrypted data can only decrypt by the key generated by the vessel 1. The vessel 2 may decrypt the encrypted data by using the key. Any other unauthorized vessel or device which may receive the encrypted data may not be able to decrypt it due to unavailability of the key. Thus, there will be a secured communication between the vessels in the aquatic environment.

The communication established between the vessels may be peer to peer (P2P) communication. Therefore, the vessel 2 may also predict and transmit an encrypt data related to the predicted location of the micro-plastics 30, amount of the micro-plastics 30, location of the vessel and a timestamp by using a key. The communication device of the vessel 1 may receive the key generated by the vessel 2 along with encrypted data of predicted location of the micro-plastics 30, amount of the micro-plastics 30, location of the vessel 2 and a timestamp from the vessel 2 and send it to the processing unit 90. The processing unit 90 may decrypt the encrypted data by using the key. Further, the processing unit 90 may receive and analyze the first set of data, the second set of data and the communicated data received from the vessel 2 to predict optimized path for the vessel 1 to collect maximum amount of micro-plastics 30 from the aquatic environment without getting delayed in reaching its destination.

In an embodiment of the present invention, the vessel 1 may comprises a display unit 100. The display unit 100 may be operationally coupled with the processing unit 90 and the GPS module 83. The display unit 100 may be configured to display the location of the vessel 1 and the optimized path for the vessel 1 to collect the maximum amount of the micro-plastics 30 from the aquatic environment. The display unit 100 may also displays the optimized path of other vessels and their predicted amount and location of the micro-plastics 30. At an event, when a vessel may take optimized path of collecting the maximum amount of micro-plastics 30, the display unit 100 may show the same. Captain of the vessel 1 may use displayed information to decide to whether to route the vessel 1 on the optimized path or not.

In another embodiment of the present invention, the processing unit 90 may comprises an AI. The AI may configured to route the vessel 1 on the optimized path. The AI may compare time that may be taken by the vessel 1 to reach destination while travelling through a pre-planned route and time that may be taken by the vessel 1 to reach destination while travelling through the optimized path. If the difference in time is so much that the vessel 1 may get delayed on the optimized path, then the AI may decide not to follow the optimized path and travel on the pre-planned path. If the difference in time is not so significant and the vessel 1 may reach the destination without getting delayed then the AI may choose the optimized path and manoeuvre the vessel 1 on the optimized path.

In another embodiment of the present invention, the captain of the vessel may have a choice to either decide manually to manoeuvre the vessel 1 on the optimized route or not or let the AI decide to manoeuvre the vessel 1 on the optimized route or not or let the AI decide.

Figure 4:
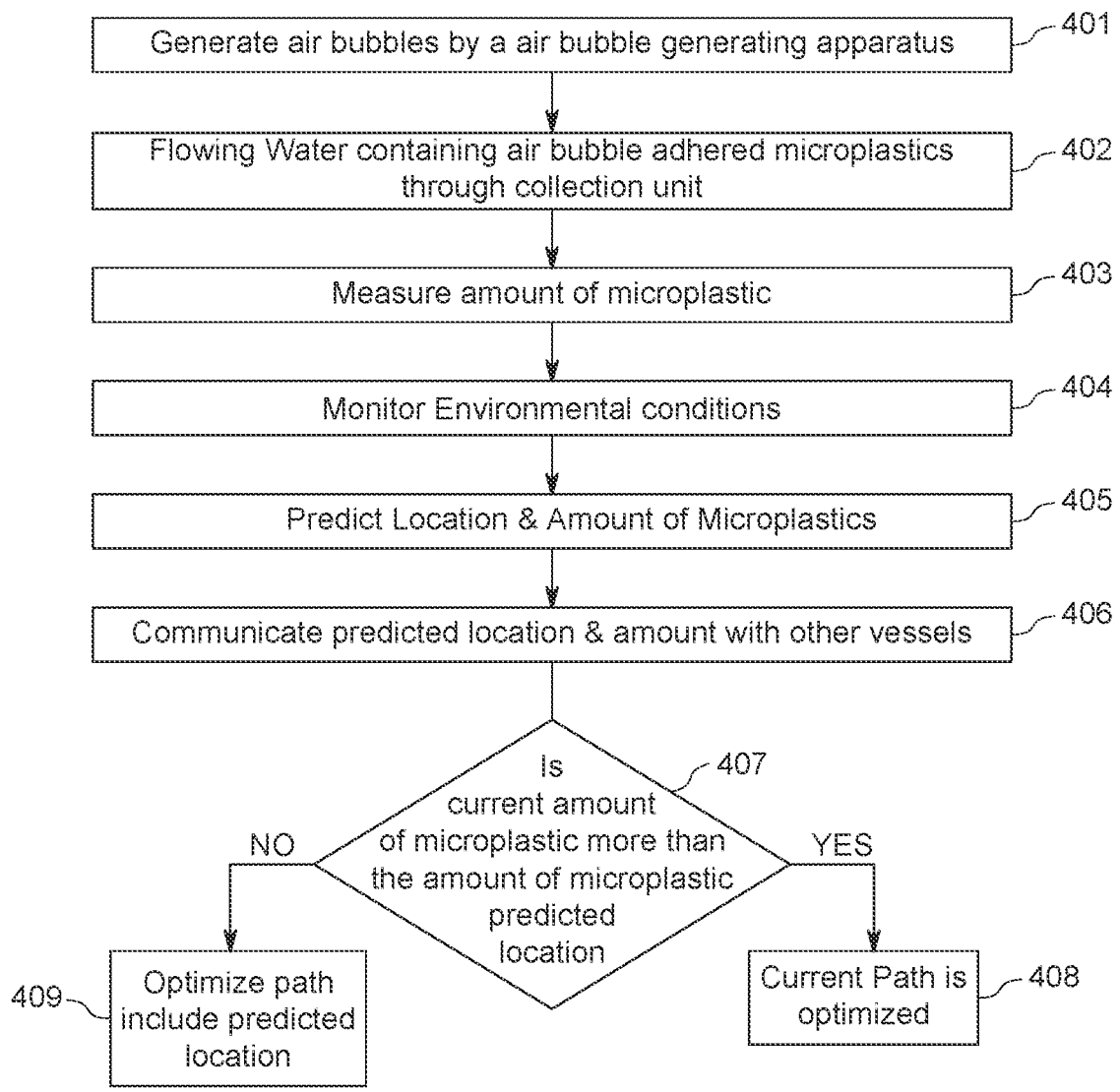
FIG. 4 illustrates a flow diagram of a method of optimizing a route of the vessel to collect maximum amount of micro-plastics from the aquatic environment as adopted in an embodiment of the invention.

FIG. 4 is a flow diagram of a method of optimizing a route of the vessel 1 to collect maximum amount of micro-plastics 30 from the aquatic environment as adopted in an embodiment of the invention. In step 401, an air bubble generating apparatus may generates air bubbles 20 ahead of a collection unit 40. Micro-plastics 30 present in the aquatic environment may get adhered to the air bubbles 20 due to their hydrophobic nature.

In step 402, water containing micro-plastics 30 adhered to the air bubble may flow through the collection unit 40. Due to buoyant forces, micro-plastics 30 adhered to the air bubble may rise upward in the collection unit 40. Rest of water along with any marine life may flow through the collection unit 40. A purifying unit 50 may be coupled to the collection unit 40 and configured to separate micro-plastics 30 from the air bubbles 20 and collects the separated micro-particle. The collected micro-plastics 30 may be removed on reaching to destination shore by empty the collected micro-plastics 30 or by an aerial vehicle (e.g., a drone) taking away the collected micro-plastics 30, etc. In another embodiment, the collected micro-plastics 30 may get burn on the vessel 1 by using ultrasonic waves or microwaves.

In an embodiment of the present invention, a first set of sensors 60 may be coupled to the vertical tube 41 of the collection unit 40. In step 403, amount of micro-plastics 30 may flow through the collection unit 40 may be measured by the first set of sensors 60. The first set of sensors 60 may generate a first set of data which corresponds to the periodic measurement of amount of the micro-plastics 30 flows through the collection unit 40.

In step 404, a second set of sensors 70 may monitor local environmental conditions. The local environmental conditions may comprises local tidal strength, local tidal currents, local tidal direction, sunlight intensity, water temperature, water salinity, local wind speed, local wind direction, barographic pressure, amount of rainfall. The second set of sensors 70 may generate a second set of data which may corresponds to the local environmental conditions. A processing unit 90 may be configured to receive the first set of data and the second set of data.

In step 405, the processing unit 90 may analyze the first set of data and the second set of data to predict amount and location of the micro-plastics 30 in the aquatic environment. As the micro-plastics 30 are very light in weight, they can easily drifted in any direction with wind or current. Therefore, the amount and location of the micro-plastics 30 present in the aquatic environments depends significantly on the local environmental conditions.

A communication device may be coupled to the processor. In step 406, the communication device may communicate location of the vessel, measured amount of the micro-plastics, environmental conditions and optimum route the predicted amount and location of the micro-plastics 30 with other vessels. The communication device may receive the location of the vessel, measured amount of the micro-plastics, environmental conditions and optimum route the predicted amount and location of the micro-plastics 30 from the other vessels. The communication device may also receive the local environmental conditions from the other vessels. The communication between vessels may be a secured peer to peer (P2P).

To establish a communication between vessels, the communication device disposed on vessel 1 may transmit an interrogation signal and an ID. The interrogation signal may be received by other vessel (Let's assume vessel 2) floating/sailing in the aquatic environment. The vessel 2 may authenticate the ID of the vessel 1 by comparing it with stored IDs in a data storage memory disposed on the vessel 2 and upon authentication may respond to the interrogation signal by transmitting a confirmation ID. The processing unit 90 disposed on the vessel 1 may authenticating the confirmation ID received from the vessel 2 by comparing with stored IDs in the data storage memory 84. Upon the authentication of the confirmed ID of the vessel 2, the processing unit 90 may encrypt data related to the predicted location of the micro-plastics 30, amount of the micro-plastics 30, location of the vessel and a timestamp and generate a key. A new key may be generate when the processing unit 90 may encrypt a new set of data. The key may be send to the vessel 2 followed by the encrypted data through the communication device disposed on the vessel 1. The encrypted data can only decrypt by the key generated by the vessel 1. The vessel 2 may decrypt the encrypted data by using the key. Any other unauthorized vessel or device which may have received the encrypted data may not be able to decrypt it due to unavailability of the key.

In similar way, the vessel 2 may also transmit a key followed by an encrypted data related to the predicted location of the micro-plastics 30, amount of the micro-plastics 30, location of the vessel and a timestamp using a public key of the vessel 1. The communication device of the vessel 1 may receive the key, the predicted amount and location of the micro-plastics 30 in the aquatic environment from the vessel 2 and send it to the processing unit 90. The processing unit 90 disposed on the vessel 1 may decrypt the encrypted data using the key.

In step 407, the processing unit 90 may receives the predicted amount and location of the micro-plastics 30 from the other vessels and compare it with the first set of data. If the amount of micro-plastics 30 flowing through the collection unit 40 is more than the predicted amount of the micro-plastics 30 at a certain location predicted by the other vessels, then the current path may be the optimized path for collecting maximum amount of micro-plastics 30 from the aquatic environment (step 408). If the amount of micro-plastics 30 flowing through the collection unit 40 is less than the predicted amount of the micro-plastics 30 at a certain location predicted by the other vessels, then the predicted location may be the optimized path for collecting maximum amount of micro-plastics 30 from the aquatic environment (step 408).

Figure 5:
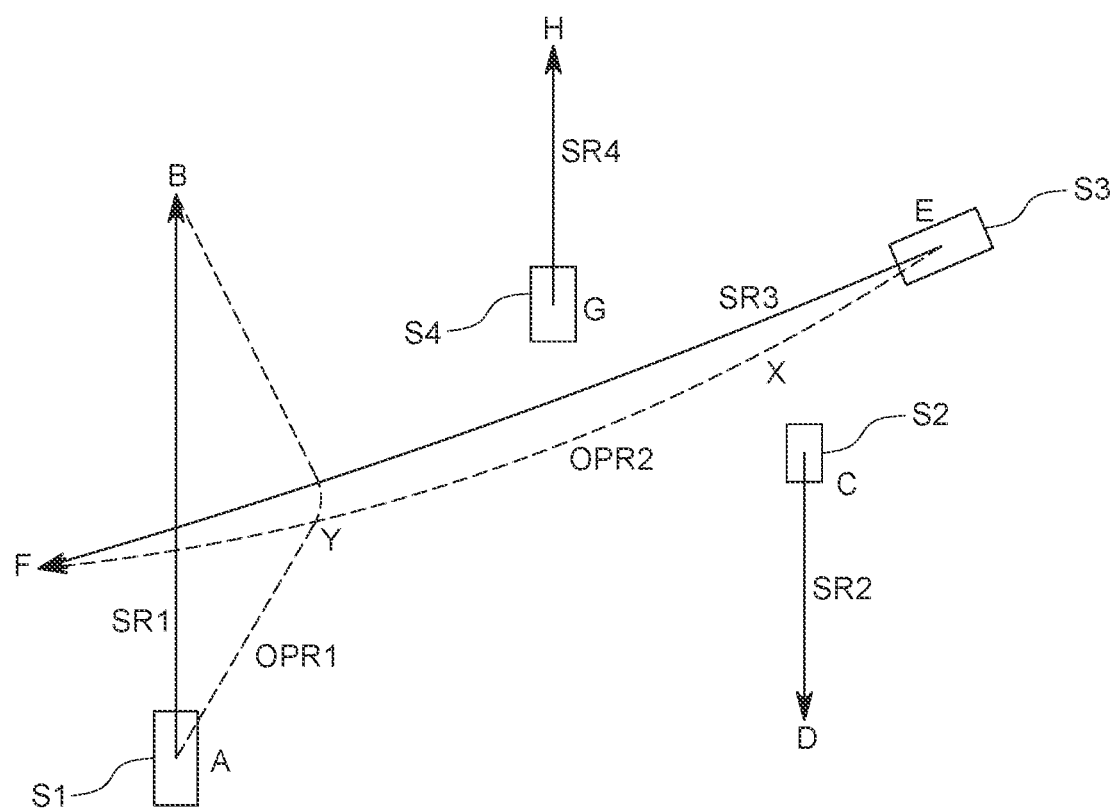
FIG. 5 illustrates a schematic diagram of a display unit displaying optimize route for the vessel for maximum collection of the micro-plastics and others vessels and their optimized route.

FIG. 5 is an exemplary embodiment of the present invention. In the exemplary embodiment, a vessel S1 may be travelling to a destination B via a route SR1. At time t=0, the vessel S1 may be located at a point A in an aquatic environment. Similarly, another vessel S2 may be travelling to a destination D via a route SR2 and at time t=0, the vessel S2 may be located at a point C in the aquatic environment. Another vessel S3 may be travelling to a destination F via a route SR3 and at time t=0, the vessel S3 may be located at a point E in the aquatic environment. Further, another vessel S4 may be travelling to a destination H via a route SR4 and at time t=0, the vessel S4 may be located at a point G in the aquatic environment. In one case, at time t=0, the vessel S1 may collects the micro-plastics at point A at a rate of M1 and predicts no displacement of micro-plastics from the location A. At time t=0, the vessel S2 may collects the micro-plastics at point C at a rate of M2 and predicts displacement of micro-plastics from the location C to a location X at time t=1. At time t=0, the vessel S3 may collects the micro-plastics at point E at a rate of M3 and predicts displacement of micro-plastics from the location E to the location X at time t=1. Similarly, at time t=0, the vessel S4 may collects the micro-plastics at point G at a rate of M4 and predicts displacement of micro-plastics from the location G to a location Y at time t=1. This information may be communicated among the vessels after authenticating the vessels in the P2P communication. As the location Y is near to the route SR1 of the vessel S1, the vessel S1 may compare the amount of collected micro-plastics M1 at location A with the amount of predicted micro-plastics at location Y. If the amount of collected micro-plastics M1 at location A is greater than the amount of predicted micro-plastics at the location Y, the system may show that the route SR1 may be the optimum route for the vessel S1. If the amount of collected micro-plastics M1 at location A is less than the amount of predicted micro-plastics at the location Y, the system may show an optimum route OPR1 which may cover location Y for the vessel S1. Similarly, for vessel S3, the system may show an optimum route OPR2 which may cover location X and location Y. As there is no predicted location of micro-plastics near route of the vessels S2 and S4, the predetermined route SR2 and SR4 may be the optimum route for the vessels S2 and S4.

The foregoing descriptions of exemplary embodiments of the present invention have been presented for purposes of illustration and description. They are not intended to be exhaustive or to limit the invention to the precise forms disclosed, and obviously many modifications and variations are possible in light of the above teaching. The exemplary embodiment was chosen and described in order to best explain the principles of the invention and its practical application, to thereby enable others skilled in the art to best utilize the invention and various embodiments with various modifications as are suited to the particular use contemplated. It is understood that various omissions, substitutions of equivalents are contemplated as circumstance may suggest or render expedient, but is intended to cover the application or implementation without departing from the spirit or scope of the claims of the present invention.

I claim:

1. A system for establishing a peer to peer (P2P) interconnection between vessels to provide an optimized and efficient route for a vessel (1), the system comprising:
   a collection unit (40) through which water containing micro-plastics (30) adhered to air bubbles (20) flows;
   a first set of sensors (60) operationally coupled to the collection unit (40) and configured to generate a first set of data by periodically measuring an amount of the micro-plastics (30) flowing in the collection unit (40);
   a second set of sensors (70) operationally coupled to the vessel (1) and configured to generate a second set of data by monitoring local environmental conditions;
   a communication device communicatively coupled to the vessel (1) and configured to communicate the first set of data and the second set of data between other vessels in an aquatic environment;
   a processing unit (90) coupled to the first set of sensors (60), the second set of sensors (70) and the communication device, wherein the processing unit (90) is configured to receive, and analyze the first set of data, the second set of data and a communicated data received from the other vessels to predict the optimum route for efficiently collecting maximum amount micro-plastics (30) from the aquatic environment.

2. The system as claimed in claim 1, further comprising:
   an air bubble generation unit (10) coupled to the vessel (1) and configured to generate air bubbles (20), wherein the micro-plastics (30) adhere to the air bubbles (20) generated by the air bubble generation unit (10);
   a purifying unit coupled to the collection unit (40) and configured to separate the micro-plastics (30) from the air bubbles (20) for collecting separated micro-plastics (30).

3. The system as claimed in claim 1, wherein the communicated data received from the other vessels comprises location of the other vessels, measured amount of the micro-plastics, environmental conditions and optimum route of the other vessels.

4. The system as claimed in claim 3, wherein the environmental conditions comprise local tidal strength, local tidal currents, local tidal direction, sunlight intensity, water temperature, water salinity, local wind speed, local wind direction, barographic pressure, amount of rainfall.

5. The system as claimed in claim 1, further comprising a display unit (100) operationally coupled to the processing unit (90) and configured to display the optimum route of the vessel (1), location of other vessels and their optimum routes.

6. The system as claimed in claim 1, further comprising a testing unit coupled to the collection unit (40), wherein the testing unit is configured to collect a sample of the water flowing through the collection unit (40) for testing chemical composition, virus and microorganisms present in the water.

7. A method for establishing a digital interconnection between vessels to provide an optimized and efficient route for a vessel (1), the method comprising:
   flowing water containing micro-plastics (30) adhered to air bubbles (20) through a collection unit (40);
   generating a first set of data at a first set of sensors (60) operationally coupled with the collection unit (40);
   generating a second set of data at a second set of sensors (70) operationally coupled with the vessel (1);
   communicating the first set of data and the second set of data among other vessels in an aquatic environment;
   receiving and analyzing at a processing unit (90), the first set of data, the second set of data, and a communicated data received from other vessels; and
   predicting at the processing unit (90), the optimum route for collecting maximum micro-plastics (30) from the aquatic environment.

8. The method as claimed in claim 7, wherein the first set of sensors (60) is configured to periodically measure amount of micro-plastics (30) flowing in the collection unit (40).

9. The method as claimed in claim 7, wherein the second set of sensors (70) is configured to monitor local environmental conditions.

10. The method as claimed in claim 7, further comprising:
   transmitting an interrogation signal and ID of the vessel (1) from a communication device disposed on the vessel (1);
   receiving the interrogation signal and ID of the vessel (1) by another vessel (2) in the aquatic environment;
   authenticating the ID of the vessel (1) by comparing the ID with prestored IDs in a data storage memory disposed on the other vessel (2);
   responding to the interrogation signal upon authentication by transmitting a confirmation ID of the other vessel (2);
   authenticating the confirmation ID received from the other vessel (2) by comparing with stored IDs in a data storage memory (84) disposed in the vessel (1);
   encrypting data of the first set of sensors, the second set of sensors, location of the vessel (1) and a timestamp done by a processing unit (90) of the vessel (1) and generating a key;
   sending the key followed by the encrypted data to the other vessel (2);
   decrypting the encrypted data by a processing unit disposed on the other vessel (2) by using the key;
   encrypting data of a first set of sensors, a second set of sensors, location of the other vessel (2) and a timestamp done by the processing unit of the other vessel (2) and generating another key;
   sending the another key followed by encrypted data to the vessel (1);
   decrypting the encrypted data by the processing unit (90) disposed on the vessel (1) by using the another key.

\* \* \* \* \*